United States Patent [19]

Furutachi et al.

[11] 3,956,339

[45] May 11, 1976

[54] 4-PYRIDINIO-5-PYRAZOLONE SALTS, PROCESS FOR THEIR PREPARATION AND THEIR USE

[75] Inventors: Nobuo Furutachi; Atsuaki Arai, both of Minami-ashigara, Japan

[73] Assignee: Fuji Photo Film Co., Ltd., Minami-ashigara, Japan

[22] Filed: Sept. 17, 1974

[21] Appl. No.: 506,808

[30] Foreign Application Priority Data

Sept. 17, 1973 Japan .............................. 48-104762

[52] U.S. Cl. .............................. 260/295 R; 96/56.5; 96/100; 260/287 D; 260/294.8 D; 260/294.8 R; 260/295 E; 260/296 R; 260/310 A

[51] Int. Cl.[2] ................ C07D 213/38; C07D 213/40

[58] Field of Search ........ 260/296 R, 310 A, 287 D, 260/295 R, 295 E, 294.8 R, 294.8 D

[56] References Cited

FOREIGN PATENTS OR APPLICATIONS 48-5,899 2/1973 Japan .................................. 260/250

OTHER PUBLICATIONS

Klingsberg, *Pyridine and Its Derivatives*, Vol. 2, pp. 2–3 and 11 to 13, Interscience Publishers, NY (1961).

Wiley et al., "Pyrazoles, Pyrazolines, Pyrazolidines, Indazoles And Condensed Rings", pp. 102 to 104, Interscience Publishers, NY, 1967.

*Chemical Abstracts*, Vol. 79, Abst. No. 146,556p (1973), (English Abst. of Japanese Patent No. 73–05,899 above cited).

*Chemical Abstracts*, Vol. 69, Abst. No. 96566n (1968), (Abst. of Stashkevich et al.).

*Primary Examiner*—John D. Randolph
*Attorney, Agent, or Firm*—Sughrue, Rothwell, Mion, Zinn & Macpeak

[57] ABSTRACT

4-Pyridinio-5-pyrazolone salts useful as dyes and particularly useful as intermediates for photographic couplers and processes for the preparation thereof.

9 Claims, No Drawings

4-PYRIDINIO-5-PYRAZOLONE SALTS, PROCESS FOR THEIR PREPARATION AND THEIR USE

BACKGROUND OF THE INVENTION

1. Field of the Invention

The present invention relates to 1,3,4-trisubstituted-5-oxo-2-pyrazoline salts in which the 4-position is substituted with a pyridine ring with the bonding being to the nitrogen atom of the pyridine ring and processes for producing the salts.

2. Description of the Prior Art

It is well-known that 1,3-disubstituted-5-oxo-2-pyrazolines are important compounds as magenta color-forming couplers for color photographic light-sensitive materials based on the subtractive process for color formation, and that these compounds are also useful as intermediates in preparing various medicines and dyes. For example, when a conventional color photographic silvr halide light-sensitive material containing a 1,3-disubstituted-5-oxo-2-pyrazoline is color developed, after exposure, the coupler couples with an oxidized para-phenylenediamine-type color developing agent to form a corresponding azomethine dye. It is well-known that such a 1,3-disubstituted-5-oxo-2-pyrazoline coupler theoretically requires for moles of silver halide as the oxidizing agent to form one mole of an azomethine dye in the color-forming coupling reaction. On the contrary, a 1,3,4-trisubstituted-5-oxo-2-pyrazoline having in the 4-position a substituent which is easily releasable on coupling with an oxidized color-developing agent can theoretically form one mole of dye using only two moles of silver halide.

For this reason, 5-oxo-2-pyrazolines having in the 4-position a releasable substituent or a precursor group which can provide a releasable substituent are particularly important compounds in the production of color photographic light-sensitive materials.

SUMMARY OF THE INVENTION

An object of the present invention is to provide 4-pyridinio-5-oxo-2-pyrazoline salts and 4-substituted pyridinio-5-oxo-2-pyrazoline salts.

Another object of the present invention is to provide a process for producing 4-pyridinio-5-oxo-2-pyrazoline salts or 4-substituted pyridinio-5-oxo-2-pyrazoline salts in high purity and in high yield using a simple procedure.

This invention thus provides a 4-pyridinio-5-pyrazolone salt represented by the following general formula (IV*a*)

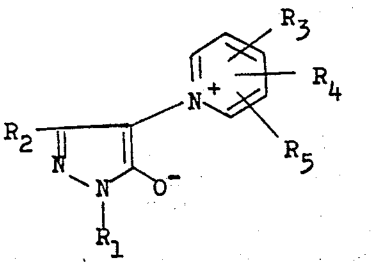
(IVa)

the general formula (IV*b*)

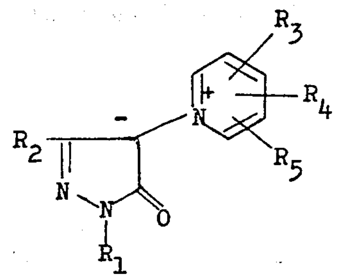
; (IVb)

the general formula (VI)

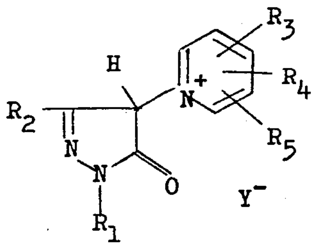
; (VI)

or a mixture thereof, wherein $R_1$ represents a hydrogen atom, a sulfamoyl group, or a group having 1 to about 40 carbon atoms; $R_2$ represents a hydrogen atom, a hydroxy group, an amino group, a sulfo group or a group having 1 to 45 carbon atoms; $R_3$, $R_4$ and $R_5$ each represents a hydrogen atom, a hydroxy group, a halogen atom, an amino group, a sulfonamido group, a sulfo group, or an alkyl group, an alkoxy group, an alkoxycarbonyl group, an aralkyl group, an aryloxy group, a carbamoyl group, a carboxy group, a carbamido group, an acylamino group, an alkylsulfonamido group, an arylsulfonamido group, an alkylamino group or an arylamino group each having 1 to 20 carbon atoms, or $R_3$ and $R_4$ can combine to form an aliphatic ring, an aromatic ring or a heterocyclic ring; and Y represents an anion.

In another embodiment of the invention, the invention provides a process for the preparation of the 4-pyridinio-5-pyrazolone salts of the General Formula (IV*a*), (IV*b*) and (VI) as defined above which comprises halogenating a 1,3-disubstituted-5-oxo-2-pyrazoline represented by the following general formula (I)

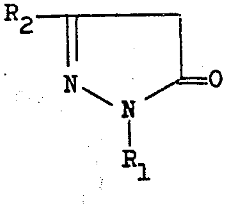
(I)

wherein $R_1$ and $R_2$ are the same as defined above to prepare a 1,3-di-substituted-4-halo-5-oxo-2-pyrazoline represented by the following general formula (II)

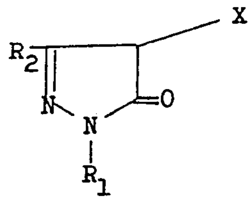

(II)

wherein $R_1$ and $R_2$ are the same as defined above and X represents a chlorine atom, a bromine atom or an iodine atom, and reacting the resulting 1,3-disubstituted-4-halo-5-oxo-2-pyrazoline of the general formula (II) with an N-heteroaromatic compound represented by the following general formula (III)

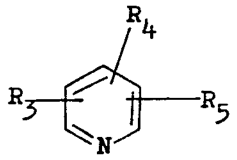

(III)

wherein $R_3$, $R_4$ and $R_5$ are the same as defined above to prepare a compound represented by the following general formula (V)

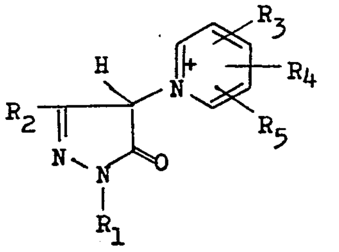

(V)

wherein $R_1$, $R_2$, $R_3$, $R_4$, $R_5$ and X are the same as defined above, which compound (i.e., the hydrogen halide salt) can be easily converted to other salts represented by the general formula (VI).

A still further embodiment of this invention comprises a process for producing the 4-pyridinio-5-pyrazoline salt of the General Formula (IV*a*), (IV*b*) or (VI) as set forth above which comprises heating a 5-oxo-2-pyrazoline represented by the following general formula (I)

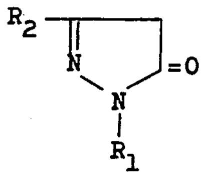

(I)

wherein $R_1$ and $R_2$ are the same as defined above, and an N-heteroaromatic compound represented by the following general formula (III)

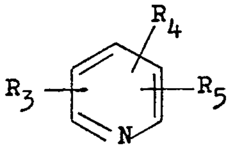

(III)

wherein $R_3$, $R_4$ and $R_5$ are the same as defined as above in the presence of an equal molar amount based on the 5-oxo-2-pyrazoline represented by the general formula (I) of a halogen to prepare the compound represented by general formula (V), which compound can be converted into other salts represented by the general formula (VI) by anion conversion.

DETAILED DESCRIPTION OF THE INVENTION

The 4-pyridinio- or 4-substituted pyridinio-5-oxo-2-pyrazolin-4-ide and 4-pyridinio- or 4-substituted pyridinio-5-oxo-2-pyrazoline salt provided according to the present invention are particularly useful as intermediates for photographic couplers. The pyridinio ring or, substituted pyridinio ring of these compounds can be converted with an appropriate reduction to the corresponding piperidino ring or substituted piperidino ring which are easily releasable on color development as in U.S. patent application Ser. No. 455,094, filed Mar. 27, 1974.

Also, the 4-pyridinio- or 4-substituted pyridinio-5-oxo-2-pyrazolin-4-ide and 4-pyridino- or 4-substituted pyridinio-5-oxo-2-pyrazoline salts have a yellow to orange color hue, and thus can be utilized as dyes for various purposes.

Many kinds of 5-oxo-2-pyrazolines which have a substituent in the 4-position are known, for example, as disclosed in U.S. Pat. No. 3,311,476. However, 1,3,4-trisubstituted-5-oxo-2-pyrazoline salts having a pyridinio group in the 4-position according to the present invention are novel compounds not described in any prior art patents or literature.

As a result of extensive investigation, 4-pyridinio salts of 5-oxo-2-pyrazolines have been developed, and these compounds can be prepared using the processes of the invention.

That is, in a first process a 1,3-disubstituted-5-oxo-2-pyrazoline represented by the following general formula (I):

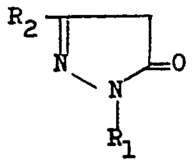

(I)

wherein $R_1$ represents a hydrogen atom, a sulfamoyl group, or a group having 1 to about 40 carbon atoms, and $R_2$ represents a hydrogen atom, a hydroxy group, an amino group, a sulfo group, or a group having 1 to about 45 carbon atoms, according to a method as described in, for example, U.S. Pat. Nos. 3,006,759 and 3,522,051, is halogenated using chlorine, bromine or iodine to prepare a 1,3-disubstituted-4-halo-5-oxo-2-pyrazoline represented by the following general formula (II):

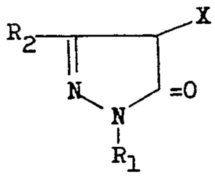
(II)

wherein $R_1$ and $R_2$ are the same as defined above: and X represents a chlorine atom, a bromine atom or an iodine atom. The compounds represented by the general formula (I) include well-known four equivalent pyrazolone magenta couplers. Representative examples of such compounds are described in U.S. Pat. Nos. 2,127,269, 2,600,788, 3,062,653, 3,337,344, 3,558,319, etc.

Suitable halogenating agents which can be used in this step are halogens such as $Cl_2$, $Br_2$ and $I_2$, sulfonyl chloride, N-chlorosuccinimide, N-bromosuccinimide, N-iodosuccinimide N-chlorobenzotriazole, etc. Suitably, the halogenating agents are used in an equimolar amount to the compound of the general formula (I), since the reaction is best controlled. An equivalent amount of the halogenating agent in excess of 1 mole is not preferred since undesired positions are halogenated. Generally, reaction temperatures in this step can range from about −10° to 50°C, preferably 0° to 20°C. The reaction is generally conducted in a solvent. Suitable solvents are protic solvents such as carboxylic acid-type solvents e.g., acetic acid, and aprotic solvents can also be used such as non-polar solvents, e.g., chloroform, carbon tetrachloride, methylene chloride, tetrahydrofuran, dioxane, etc. The amount of the solvents to be employed is generally about 10% by volume per weight of the compound of the general formula (I). After the reaction has been completed, the solvent is evaporated to dryness. The thus obtained 1,3-di-substituted-4-halogeno-5-oxo-2-pyrazoline (II) is sufficiently pure to be used, but if desired it can be recrystallized from suitable solvents. Where acetic acid is used as a solvent, the reaction mixture can be poured into ice-water and then filtered. The solid product is dried and recrystallized for recovery. The resulting 1,3-disubstituted-4-halo-5-oxo-2-pyrazoline of the general formula (II) is then reacted with an N-heteroaromatic compound represented by the following general formula (III):

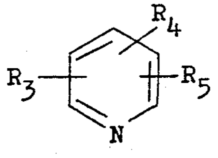
(III)

wherein $R_3$, $R_4$ and $R_5$ each represents a hydrogen atom, a hydroxy group, a halogen atom, an amino group, a sulfonamido group, a sulfo group, or an alkyl group, an aralkyl group, an alkoxy group, an alkoxycarbonyl group, an aryloxy group, a carboxy group, a carbonamido group, a carbamoyl group, an acylamido group, an alkylsulfonamido group, an arylsulfonamido group, an alkylamino group or an arylamino group each having 1 to 20 carbon atoms or $R_3$ and $R_4$ can combine to form an aliphatic ring, an aromatic ring or a heterocyclic ring.

In this step of the synthesis a suitable molar ratio of the compound of the general formula (II) to the compound of the general formula (III) can suitably range from about 1:2 to 1:20, by weight, preferably 1:4 to 1:10. Suitable temperature ranges for conducting this step of the synthesis are of from about 10° to 100°C, preferably 20° to 60°C. The reaction can be conducted in the absence of a solvent since the compound of the general formula (III) per se acts as a solvent. In such a case the compound of the general formula (III) is used in an amount of about 5 to 50% by weight to the total weight of the reactants (II + III). However, solvents, e.g., alcohols such as methanol or ethanol, benzene, acetonitrile, chloroform, etc., can, of course, be effectively used. In this case the solvent is suitably employed in an amount of from about 20 to 500 ml per 10 g of the compound of the general formula (II). When the reaction of this step is conducted in the absence of a solvent, the product is extracted from the reaction mixture using a suitable solvent such as diethyl ether, ethyl acetate, chloroform, etc., washed with water, dried and recrystallized. Where the reaction is conducted using a solvent, the solvent is evaporated. After extracting with a suitaable solvent such as diethyl ether, ethyl acetate, chloroform, etc., the extract is dried over sodium sulfate. The solvent is evaporated off to obtain the product, which can be recrystallized, if desired.

According to this process, the 4-halo-5-oxo-2-pyrazoline which is obtained from the 5-oxo-2-pyrazoline need not be isolated in a pure state. That is, when a desired N-heteroaromatic compound is reacted with the crude 4-halogenated product under heating, a 4-N-heteroaromatic ylide of the 5-oxo-2-pyrazoline can be isolated at this stage with ease as yellow crystals without any loss, since the resulting ylide has an extremely low solubility.

A second process comprises heating a 5-oxo-2-pyrazoline represented by the general formula (I) and a N-heteroaromatic compound represented by the general formula (III) in the presence of an equimolar amount of a halogen based on the amount of the 5-oxo-2-pyrazoline represented by the general formula (I). Preferred halogens are bromine and iodine. This reaction can be conducted in the presence of a solvent, e.g., alcohols such as methanol, ethanol, etc., acetonitrile, chloroform, benzene, or the like. The solvent is generally used in an amount of about 20 to about 500 ml, preferably 50 to 100 ml, to about 10 g of the compound of the general formula (I). The reaction temperatures generally range from about 20° to about 200°C, preferably while heating to reflux on a steam bath. An advantage of this process is that the process is particularly suitable for applying to a 5-oxo-2-pyrazoline in which there is a tendency for two halogen atoms to be introduced into the 4position when the 5-oxo-2-pyrazoline is halogenated by the first process.

In these two processes described above, prolonged heating of the reaction mixture is sufficient to consume the starting material, the 5-oxo-2-pyrazoline of the general formula (II), completely, and therefore, isolating the remaining starting materials is unnecessary. These reactions can be followed by TLC in order to determine the complete consumption of the starting materials, and the reaction and its progress can be controlled in this manner.

Under usual conditions, the product is obtained as an inner salt (an N-heteroaromatic ylide type) represented by the following general formula (IV*a*) or (IV*b*):

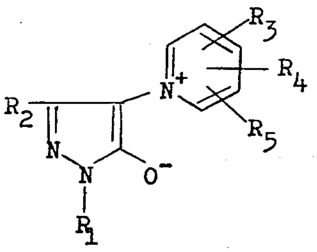

(IVa)

or

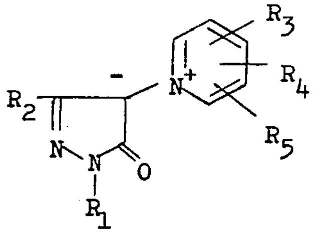

(IVb)

wherein $R_1$, $R_2$, $R_3$, $R_4$, and $R_5$ are the same as defined above. The above compounds of the general formulae (IV*a*) and (IV*b*) are tautomeric forms. However, in some cases, a corresponding hydrogen halide salt thereof represented by the following general formula

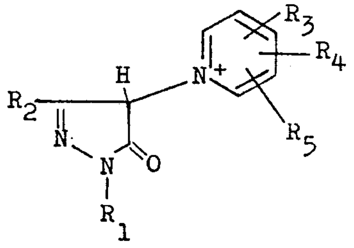

$X^-$ (V)

wherein $R_1$, $R_2$, $R_3$, $R_4$, $R_5$ and X are the same as defined above, is present in the product. The inner salt represented by the general formula (IV*a*) or (IV*b*) and the hydrogen halide salt represented by the general formula (V) can be converted into each other or alternatively into the salt represented by the general formula (VI) by well-known anion conversion methods.

The 5-oxo-2-pyrazoline-4-pyridinium salt derivatives of the present invention include the compounds represented by the above-described general formulae (IV*a*), (IV*b*), (V) and (VI).

The compounds represented by the above-described general formula (I) which can be used in the present invention are described in detail below.

Suitable groups having 1 to about 40 carbon atoms represented by $R_1$ in the general formula (I) include, for example, an alkyl group, an alkoxycarbonyl group, a carboxy group or an aryl group such as a phenyl group or a phenyl group having one or more substituents such as an alkyl group (e.g., having 1 to 30 carbon atoms), an alkoxy group (e.g., having 1 to 30 carbon atoms), an aryl group (e.g., phenyl, naphthyl, etc.), an aryloxy group (e.g., phenoxy, naphthoxy, or a phenoxy or naphthoxy substituted with a group having 1 to 10 carbon atoms), a halogen atom, an alkoxycarbonyl group (e.g., having 1 to 30 carbon atoms), an acylamino group (e.g., having 1 to 30 carbon atoms), a carbamoyl group (e.g., having 1 to 30 carbon atoms), a sulfo group, an alkylsulfonamido group (e.g., having 1 to 30 carbon atoms), an arylsulfonamido group (e.g., phenylsulfonamido, naphthylsulfonamido, or phenyl- or naphthylsulfonamido having a substituent containing 1 to 20 carbon atoms), a sulfamoyl group, a cyano group, a nitro group, and a carboxy group, etc.

Suitable groups having 1 to about 45 carbon atoms represented by $R_2$ include, for example, an alkyl group (e.g., having 1 to 45 carbon atoms), an aryl group (e.g., phenyl, naphthyl or substituted phenyl or substituted naphthyl substituted with a substituent containing 1 to 30 carbn atoms), an alkoxy group (e.g., having 1 to 45 carbon atoms), an aryloxy group, an alkoxycarbonyl group (e..g., having 1 to 40 carbon atoms), an alkylamino group (e.g., having 1 to 45 carbon atoms), a cycloalkylamino group (e.g., having 3 to 8 carbon atoms such as cyclopentylamino, cyclohexylamino, cycloheptylamino, and cycloalkylamino having a substituent group containing 1 to 30 carbon atoms), a dialkylamino groupp (e.g., in which the alkyl moiety has 1 to 20 carbon atoms), a diarylamino group (e.g., diphenylamino, dinaphthylamino, substituted diphenylamino and substituted dinaphthylamino having a substituent containing 1 to 15 carbon atoms), an arylamino group (e.g., an amino group containing an aryl substituent having 6 to 45 carbon atoms, e.g., anilino), an acylamino group (e.g., an amino group containing an acyl substituent having 1 to 45 carbon atoms), an N-alkylacylamino group (e.g., an N-alkylacylamino group in which the acyl moiety has 1 to 30 carbon atoms and the alkyl moiety has 1 to 10 carbon atoms), a carbamoyl group (e.g., having 1 to 45 carbon atoms), an N-arylacylamino group, (e.g., a phenylacylamino, a naphthylacylamino, a substituted phenylacylamino group containing a phenyl substituent having 1 to 10 carbon atoms, in which the acyl moiety has 1 to 20 carbon atoms), a ureido group (e.g., ureido, N-alkylureido, N-phenylureido, N-naphthyl ureido having 1 to 45 carbon atoms and N-substituted phenyl ureido, N-substituted naphthyl ureido having 1 to 20 carbons in the substituent group, and N-cycloalkyl ureido having 5 to 30 carbon atoms), a diacyl amino group (e.g., a diacylamino group having 1 to 20 carbon atoms in each acyl substitutent), a carboxy group etc.

As the pyradine ring-containing compounds represented by the above-described general formula (III), any pyridine ring-containing compounds which are capable of reacting with a 4-halo-5-oxo-2-pyrazoline to form a pyridinium salt or which are capable of reacting with a 5-oxo-2-pyrazoline in the presence of a halogen to form a pyridinium salt can be used as a starting material in the present invention. Since the reaction site is located at the nitrogen atom of the pyridine ring, $R_3$, $R_4$ and $R_5$ are not particularly limited and can vary.

Suitable anions for Y include a chlorine atom, a bromine atom, an iodine atom, a perchlorate group, a periodate group or a p-toluene sulfonate group.

Preferred examples of the compounds represented by the general formula (III) are those in which $R_3$, $R_4$ and $R_5$ each represents, for example, a hydrogen atom, a hydroxy group, a halogen atom, an amino group, a sulfamido group, a sulfo group and a group containing 1 to 20 carbon atoms and more specifically an alkyl group (e.g., containing 1 to 20 carbon atoms), an aralkyl group (e.g., containing 1 to 20 carbon atoms), an alkoxy group (e.g., containing 1 to 20 carbon atoms), an alkoxycarbonyl group (e.g., containing 1 to 20 carbon atoms), an aryloxy group (e.g., phenoxy, naphthoxy, substituted phenoxy containing a substituent having 1 to 14 carbon atoms, substituted naphthoxy containing a substituent having 1 to 10 carbon atoms), a carboxy group, a carbonamido group (e.g., having 1 to 20 carbon atoms), an acylamino group (e.g., in which the acyl moiety has 1 to 20 carbon atoms), an alkylsulfonamido group (e.g., having 1 to 20 carbon atoms), an arylsulfonamido group (e.g., phenylsulfonamido, naphthylsulfonamido, substituted phenylsulfonamido in which the substituent has from 1 to 14 carbon atoms, substituted naphthylsulfonamido in which the substitutent has from 1 to 10 carbon atoms), an alkylamino group (e.g., having 1 to 20 carbon atoms), an arylamino group (e.g., phenylamino, naphthylamino, substituted phenylamino having a substituent containing 1 to 14 carbon atoms, substituted naphthylamino having a substituent containing 1 to 10 carbon atoms), etc. $R_3$ and $R_4$ can also fuse to form an aliphatic ring, an aromatic ring, a heterocyclic ring, more specifically to form, a cyclopentane, cyclohexane, cycloheptane, benzene, and substituted benzene ring which is substituted with a halogen atom, an amino group, a hydroxy group, a sulfo group, a carboxy group, a sulfonamido group, or an alkyl, alkoxy, acylamino, alkylamino, or arylamino group, each as above defined or a pyridine ring, a dihydrofuran ring, a dihydrothiophene ring, or a thiophene ring (especially, a 5-or 6-membered ring).

Specific examples of compounds containing a pyridine ring are, for example, pyridine, α-picoline, γ-picoline, 3-butylpyridine, 4-propylpyridine, 3-amylpyridine, 3-benzylpyridine, 4-β-phenylethylpyridine, 4-β-(4-methoxyphenyl)ethylpyridine, 4-β-(4-hydroxy-3-methoxy-phenyl)ethylpyridine, 3,5-lutidine, 3-ethyl-4-methylpyridine, 3-methylquinoline, 3,4-dimethylquinoline, 7-chloro-3-methylquinoline, 2,4,6-trimethylquinoline, 1,2-bis(4-pyridyl)ethane, 3-bromopyridine, 2,4,6-collidine, 3,4-lutidine, 3,5-dichloropyridine, 4,4-dipyridyl, 4-phenylpyridine, isoquinoline, phenanthridine, 4-methanolpyridine, 3-acetylaminopyridine and the like.

Specific examples of the 1,3-disubstituted-4-pyridinium-5-pyrazolone salts which can be produced according to the present invention are described below. However, the present invention is not to be interpreted as being limited only to these examples.

COMPOUND 1

1-(2,4,6-Trichlorophenyl)-3-{3-[(2,4-di-tert-amylphenoxy)-acetamido]benzamido}-4-(1-pyridinio)-5-oxo-2-pyrazolin-4-ide

COMPOUND 2

1-(2,4,6-Trichlorophenyl)-3-{3-[α-(2,4-di-tert-amylphenoxy)-butyramido]benzamido}-4-(1-pyridinio)-5-oxo-2-pyrazoline bromide

COMPOUND 3

1-(2,4,6-Trichlorophenyl)-3-{3-[(2,4-di-tert-amylphenoxy)-acetamido]benzamido}-4-(3-ethyl-4-methyl-1-pyridinio)-5-oxo-2-pyrazolin-4-ide

COMPOUND 4

1-(2,6-Dichloro-4-methoxyphenyl)-3-{3-[(2,4-di-tert-amyl-phenoxy)acetamido]benzamido}-4-(1-pyridinio)5-oxo-2-pyrazolin-4-ide

COMPOUND 5

1-(2,6-Dichloro-4-methylphenyl)-3-{[α-(2,4-di-tert-amylphenoxy)]butryamido}-4-(1-pyridinio)-5-oxo-2-pyrazoline bromide

COMPOUND 6

1-(2,6-Dichloro-4-methoxyphenyl)-3-{3-[α-(2,4-di-tert-amylphenoxy)butyramido]phenylureido}-4-(1-pyridinio)-5-oxo-2-pyrazolin-4-ide Compound 7

1-(2,4,6-Trichlorophenyl)-3-n-butyloxy-4-(2-isoquinilinio)-5-oxo-2-pyrazolin-4-ide Compound 8

1-(2,4,6-Trichlorophenyl)-3-(2-chloro-5-dodecyloxycarbonylanilino)-4-(1-pyridinio-4-oxo-2-pyrazolin-4-ide Compound 9

1-Phenyl-3-methyl-4-(1-pyridinio)-5-oxo-2-pyrazolin-4-ide

COMPOUND 10

1-(2,4,6-Trichlorophenyl)-3-{2-chloro-5-[α-(2,4-di-tert-amylphenoxy)butyramido]anilino}-4-(1-pyridinio)-5-oxo-2-pyrazoline iodide

COMPOUND 11

1-(4-Acetamidophenyl)-3-ethoxy-4-(3-ethyl-4-methyl-1-pyridinio)-5-oxo-2-pyrazolin-4-ide

COMPOUND 12

1-(2,4,6-Trichlorophenyl)-3-{3-[α-(2,4-di-tert-amylphenoxy)-butyramido]benzamido}-4-(2-isoquinolinio)-5-oxo-2-pyrazoline iodide

COMPOUND 13

1-(2-Chloro-4,6-dimethylphenyl)-3-{3-[γ-(3-pentadecyl-phenoxy)butyramido]benzamido}-4-(1-pyridinio)-5-oxo-2-pyrazolin-4-ide

COMPOUND 14

1-(2,4,6-Trichlorophenyl)-3-cyclohexylamino-4-(1-pyridinio)-5-oxo-2-pyrazoline iodide

COMPOUND 15

1-{4-[α-(3-n-Pentadecylphenoxy)butyramido]phenyl}-3-benzamido-4-(1-pyridinio)-5-oxo-2-pyrazolin-4-ide

COMPOUND 16

1-Phenyl-3-(3-n-tetradecanamido)anilino-4-(4-propylpyridinio)-5-oxo-2-pyrazolin-4-ide

COMPOUND 17

1-(2,4,6-Trichlorophenyl)-3-(4-n-tetradecanamido)anilino-4-(3,5-dimethyl-1-pyridinio)-5-oxo-2-pyrazonlin-4-ide

COMPOUND 18

1-(2,4,6-Trichlorophenyl)-3-[2-chloro-5-(n-tetradecanamido)-anilino]-4-(1-pyridinio)-5-oxo-2-pyrazolin-4-ide

COMPOUND 19

1-(2,4,6-Trichlorophenyl)-3-(3-n-tetradecanamido)-benzamido-4-[2-(5,6,7,8-tetrahydroisoquinolinio)]-5-oxo-2-pyrazoline-4-ide

COMPOUND 20

1-(4-chlorophenyl)-3-{3-[(3-n-pentadecylphenoxy)acetamido]-anilino}-4-[2-(2,7-naphthyridinio)]-5-oxo-2-pyrazoline-4-ide The present invention will now be illustrated in greater detail by reference to the following examples which, however, are not intended to be interpreted as limiting the present invention in any way. Unless otherwise indicated, all parts, percents, ratios and the like are by weight.

EXAMPLE 1

Production of 1-(2,4,6-Trichlorophenyl)-3-{3-[(2,4-di-tert-amylphenoxy)acetamido]benzamido}-4-(1-pyridinio)-5-oxo-2-pyrazolin-4-ide (Compound 1)

To a solution containing 90 g of 1-(2,4,6-trichlorophenyl)-3-{3-[(2,4-di-tert-amylphenoxy)acetamido]-benzamido}-5-pyrazolone in 500 ml of a solvent mixture of chloroform and carbon tetrachloride (3:2 by volume ratio), 21 g of bromine was added dropwise maintaining the reaction temperature less than 20°C. After the completion of the reaction, the solvent was distilled off under reduced pressure. To the gummy residue, without crystallizing, 200 ml of pyridine was added and the mixture was heated on a steam bath for 30 minutes, then allowed to stand at room temperature for one day. The excess pyridine was distilled off under reduced pressure, the residual solid material was recrystallized from ethanol to give 82 g of Compound 1 having a melting point of 178° to 180°C.

Elemental Analysis: Calcd. for $C_{39}H_{40}N_5O_4Cl_3$: C(62.5%); H(5.35%); N(9.35%). Found: C(62.3%);

H(5.36%); N(9.30%). IR (Nujol mull): 3210 $cm^{-1}$, 1703 $cm^{-1}$, 1675 $cm^{-1}$.

EXAMPLE 2

Production of 1-(2,4,6-Trichlorophenyl)-3-{3-[α-(2,4-di-tert-amylphenoxy)butyramido]benzamido}-4-(1-pyridinio)-5-oxo-2-pyrazoline bromide (Compound 2)

35 g Of 1-(2,4,6-trichlorophenyl)-3-{3-[α-(2,4-di-tert-amylphenoxy)butyramido]benzamido}-5-pyrazolone was brominated and reacted with pyridine in the same manner as described in Example 1. After removing the excess pyridine under reduced pressure, the residue was dissolved in excess ethanol, and to the solution 15 ml of 47% hydrobromic acid was added and then the solvent was distilled off under reduced pressure. The residue was recrystallized from ethanol to give 2 g of Compound 2 as yellow crystals.

Elemental Analysis: Calcd. for $C_{41}H_{44}N_5O_4Cl_3 \cdot HBr$: C(57.4%); H(5.24%); N(8.16%). Found C(57.2%); H(5.26%); N(8.17%). IR (Nujol mull): 3200 $cm^{-1}$, 1700 $cm^{-1}$, 1680 $cm^{-1}$.

EXAMPLE 3

Production of 1-(2,4,6-Trichlorophenyl)-3-{3-[(2,4-di-tert-amylphenoxy)acetamido]benzamido}-4-(3-ethyl-4-methyl-1-pyridinio)-5-oxo-2-pyrazolin-4-ide (Compound 3)

10 g Of 1-(2,4,6-trichlorophenyl)-3-{3-[(2,4-di-tert-amylphenoxy)acetamido]benzamido}-4-bromo-5-pyrazolone and 6.4 g of β-collidine were refluxed in 100 ml of ethanol for 5 hours. After cooling, the resulting crystals were washed with water and dried, and recrystallized from ethanol to give 10 g of Compound 3 having a melting point of 162° to 165°C.

Elemental Analysis: Calcd. for $C_{42}H_{46}N_5O_4Cl_3$: C(63.7%); H(5.81%); N(8.84%). Found: C(63.5%); H(5.80%); N(8.80%). IR (Nujol mull): 3200 $cm^{-1}$, 1710 $cm^{-1}$, 1680 $cm^{-1}$, 1595 $cm^{-1}$

EXAMPLE 4

Production of 1-(2,4,6-Trichlorophenyl)-3-{3-[α-(2,4-di-tert-amylphenoxy)butyramido]benzamido}-4-(2-isoquinolinio)-5-oxo-2-pyrazoline iodide (Compound 12)

17 g Of 1-(2,4,6-trichlorophenyl)-3-{3-[α-(2,4-di-tert-amylphenoxy)butyramido]benzamido}-5-pyrazolone was brominated in the same manner as described in Example 2. To the crude brominated compound, 9.7 g of isoquinoline and 75 ml of ethanol were added, and the mixture was refluxed on a steam bath until the disappearance of the brominated compound was complete as indicated by thin layer chromatography, and then allowed to stand at room temperature for 1 day. After removing the solvent under reduced pressure, the residue was dissolved in ethyl acetate and the solution was washed with water, and then the ethyl acetate was distilled off under reduced pressure. The residue was dissolved in excess ethanol, and to the solution 10 ml of 57% hydroiodic acid was added. The solution was concentrated under reduce pressure until the appearance of crystals was observed, and allowed to stand at a cool temperature for 1 day, then filtered to give 12 g of Compound 12 having a melting point of 184° to 185°C.

Elemental Analysis: Calcd. for $C_{45}H_{46}N_5O_4Cl_3 \cdot HI$: C(56.6%); H(4.93%); N(7.34%). Found: C(56.6%);

H(5.00%); N(7.32%). IR (Nujol mull): 3240 $cm^{-1}$, 1710 $cm^{-1}$, 1685 $cm^{-1}$

EXAMPLE 5

Production of 1-(2,4,6-Trichlorophenyl)-3-[2-chloro-5-(n-tetradecanamido)anilino]-4-(1-pyridinio)-5-oxo-2-pyrazolin-4-ide (Compound 18)

A mixture of 7.1 g of 1-(2,4,6-trichlorophenyl)-3-[2-chloro-5-(n-tetradecanamido)anilino]-5-pyrazolone, 2.5 g of iodine and 100 ml of pyridine was heated on a steam bath for 5 hours. After cooling, the reaction mixture was poured into a large volume of ice water. The precipitate was collected by filtration and dried. The powder was recrystallized from a solvent mixture of hexane and ethyl acetate to give 4.8 g of Compound 18 as yellow crystals having a melting point of 124° to 128°C.

Elemental Analysis: Calcd. for $C_{34}H_{39}N_5O_2Cl_4$: C(59.0%); H(5.64%); N(10.1%). Found: C(59.1%); H(5.63%); N(10.0%). IR (Nujol mull): 1685 $cm^{-1}$, 1605 $cm^{-1}$.

While the invention has been described in detail and with reference to specific embodiments thereof, it will be apparent to one skilled in the art that various changes and modifications can be made therein without departing from the spirit and scope thereof.

What is claimed is:

1. A 4-pyridinio-5-pyrazolone salt represented by the following formula (IV*a*)

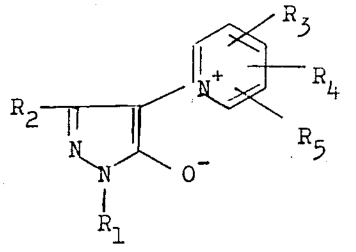

(IVa)

the formula (IV*b*)

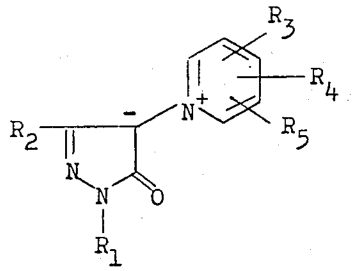

(IVb)

the formula (VI)

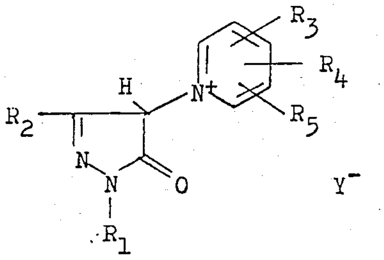

(VI)

or a mixture thereof, wherein $R_1$ represents a hydrogen atom; sulfamoyl; alkyl having 1 to 40 carbon atoms, alkoxycarbonyl having 1 to 40 carbon atoms, carboxy having 1 to 40 carbon atoms, aryl having 1 to 40 carbon atoms, aryl comprising phenyl substituted with alkyl having 1 to 30 carbon atoms, alkoxy having 1 to 30 carbon atoms, aryloxy comprising phenoxy or naphthoxy, or phenoxy or naphthoxy having a substituent group having 1 to 10 carbon atoms, acylamino having 1 to 30 carbon atoms, carbamoyl having 1 to 30 carbon atoms, alkylsulfonamido having 1 to 30 carbon atims, arylsulfonamido comprising phenylsulfonamido or naphthylsulfonamido, and arylsulfonamido comprising phenylsulfonamido or naphthylsulfonamido having a substituent group having 1 to 20 carbon atoms; $R_2$ represents a hydrogen atom, hydroxy, amino, sulfo, alkyl having 1 to 45 carbon atoms, aryl comprising phenyl or naphthyl, or phenyl or naphthyl having a substituent group having 1 to 30 carbon atoms, alkoxy having 1 to 45 carbon atoms, aryloxy having 1 to 45 carbon atoms, alkoxycarbonyl having 1 to 40 carbons atoms, alkylamino having 1 to 45 atoms, cycloalkylamino having 3 to 8 carbon atoms and comprising cyclopentylamino, cyclohexylamino, and cycloheptylamino, cycloakylamino having 3 to 8 carbon atoms having a substituent group having 1 to 30 carbon atoms, dialkylamino wherein the alkyl 1 to 20 carbon atoms, diarylamino comprising diphenylamino or dinaphthylamino, or diphenylamino or dinaphthylamino having a substituent group having 1 to 15 carbon atoms, arylamino wherein the aryl has 6 to 45 carbon atoms, acylamino wherein the acyl has 1 to 45 carbon atoms, N-alkylacylamino wherein the acyl has 1 to 30 carbon atoms and the alkyl has 1 to 10 carbon atoms, carbamoyl having 1 to 45 carbon atoms, N-arylacylamino comprising phenyl-acylamino or naphthylacylamino, or phenylacylamino having a substituent group containing phenyl having 1 to 10 carbon atoms and wherein the acyl has 1 to 20 carbon atoms, ureido comprising ureido, N-alkylureido, N-phenylureido, N-naphthyl ureido having 1 to 45 carbon atoms and N-substituted phenyl ureido, N-substituted naphthyl ureido having 1 to 20 carbon atoms in the substituent group and and N-cycloalkyl ureido having 5 to 30 carbon atoms, diacyl amino wherein the acyl has 1 to 20 carbon atoms, and carboxy; $R_3$, $R_4$ and $R_5$ each represents a hydrogen atom, hydroxy, a halogen atom, amino, sulfonamido, sulfo, alkyl having 1 to 20 carbon atoms, alkoxy having 1 to 20 carbon atoms, alkoxycarbonyl having 1 to 20 carbon atoms, aralkyl having 1 to 20 carbon atoms, aryloxy comprising phenoxy or naphthoxy, or phenoxy having a substituent group having 1 to 14 carbon atoms or napthoxy having a substituent group having 1 to 10 carbon atoms, carboxy, carbamoyl having 1 to 20 carbon atoms, carbamido having 1 to 20 carbon atoms, acylamino wherein the acyl has 1 to 20 carbon atoms, alkylsulfonamido having 1 to 20 carbon atoms, arylsulfonamido comprising phenylsulfonamido or naphthylsulfonamido, or phenylsulfonamido having a substituent group having 2 to 14 carbon atoms or naphthylsulfonamido having a substituent group having 1 to 10 carbon atoms, alkylamino having 1 to 20 caron atoms, arylamino comprising phenylamino or naphthylamino, or phenylamino having a substituent group having 1 to 14 carbon atoms or naphthylamino having a substituent group having 1 to 10 carbon atoms, or $R_3$ and $R_4$ can combine to form cyclopentane, cyclohexane, cycloheptane, benzene, benzene substituted with a halogen atom, amino, hydroxy, sulfo, carboxy, sulfonamido or alkyl, alkoxy, acylamino, alkylamino or arylamino as defined for $R_2$, pyridine ring, dihydrofuran ring, dihydrothiophene ring or a thiophene ring; and Y represents chlorine, bromine, iodine, perchlorate, periodate or p-toluene sulfonate.

2. The 4-pyridinio-5-pyrazolone salt of claim 1, wherein the salt has the following formula (IV*a*)

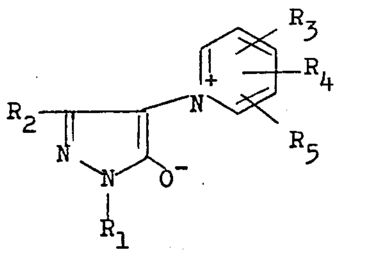

(IVa)

or the formula (IV*b*)

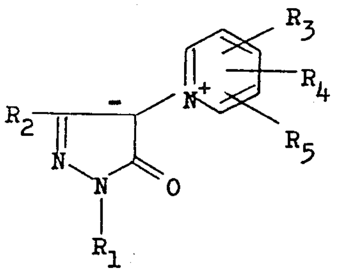

(IVb)

wherein $R_1$, $R_2$, $R_3$, $R_4$ and $R_5$ are the same as defined in claim 1.

3. The 4-pyridinio-5-pyrazolone salt of claim 1, wherein the salt has the following formula (V)

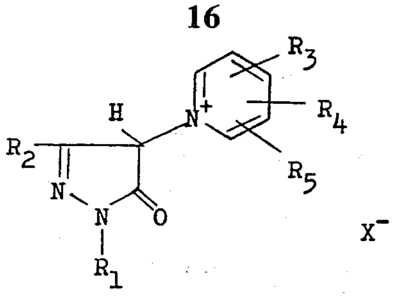

(V)

wherein $R_1$, $R_2$, $R_3$, $R_4$, and $R_5$ are the same as defined in claim 1, and X is a chlorine atom, a bromine atom or an iodine atom.

4. The 4-pyridinio-5-pyrazolone salt as claimed in claim 1, wherein $R_1$ is said alkyl, said aryl, said carboxy, or said alkoxy-carbonyl.

5. The 4-pyridinio-5-pyrazolone salt of 1-(2,4,6-trichlorophenyl)-3- 3-[(2,4-di-tert-amylphenoxy)acetamido]benzamido -4-(1-pyridinio)-5-oxo-2-pyrazoline-4-ide.

6. The 4-pyridinio-5-pyrazolone salt of 1-(2,4,6-trichlorophenyl)-3- 3-[α-(2,4-di-tert-amylphenoxy)butryramido]benzamido -4-(1-pyridinio)-5-oxo-2-pyrazoline bromide.

7. The 4-pyridinio-5-pyrazolone salt of 1-(2,4,6-trichlorophenyl)-3-- -[(2,4-di-tert-amylphenoxy-acetamido]benzamido - 4-(3-ethyl-4-methyl-1-pyridinio)-5-oxo-2-pyrazolin-4-ide.

8. The 4-pyridinio-5-pyrazolone salt of 1-(2,4,6-trichlorophenyl)-3- 3-[α-(2,4-di-tert-amylphenoxy)-butyramido]benzamido -4-(2-isoquinolinio)-5-oxo-2-pyrazoline iodide.

9. The 4-pyridinio-5-pyrazolone salt of 1-(2,4,6-trichloropehnyl)-3-[2-chloro-5-(n-tetradecanamido)anilinio]-4-(1-pyridinio)-5-oxo-2-pyrazoline-4-ide.

* * * * *